(12) United States Patent
Van Dijk et al.

(10) Patent No.: US 8,314,407 B2
(45) Date of Patent: Nov. 20, 2012

(54) OPTICAL ILLUMINATION APPARATUS FOR ILLUMINATING A SAMPLE WITH A LINE BEAM

(75) Inventors: Erik Martinus Hubertus Petrus Van Dijk, Eindhoven (NL); Sjoerd Stallinga, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 154 days.

(21) Appl. No.: 12/743,824

(22) PCT Filed: Nov. 19, 2008

(86) PCT No.: PCT/IB2008/054862
§ 371 (c)(1),
(2), (4) Date: May 20, 2010

(87) PCT Pub. No.: WO2009/066254
PCT Pub. Date: May 28, 2009

(65) Prior Publication Data
US 2010/0288942 A1 Nov. 18, 2010

(30) Foreign Application Priority Data
Nov. 23, 2007 (EP) .................................. 07121415

(51) Int. Cl.
*G21K 5/00* (2006.01)
(52) U.S. Cl. .................. 250/458.1; 250/459.1
(58) Field of Classification Search ............... 250/458.1, 250/459.1
See application file for complete search history.

(56) References Cited

U.S. PATENT DOCUMENTS

| | | | |
|---|---|---|---|
| 3,013,467 A | 12/1961 | Minsky | |
| 5,054,926 A | 10/1991 | Dabbs et al. | |
| 5,467,335 A | 11/1995 | Braat | |
| 6,108,138 A * | 8/2000 | Ophey et al. ................. | 359/711 |
| 6,181,474 B1 | 1/2001 | Ouderkirk et al. | |
| 6,683,838 B2 * | 1/2004 | Jutte ........................ | 369/112.24 |
| 7,009,928 B2 * | 3/2006 | Jutte et al. ................ | 369/112.05 |
| 2003/0151735 A1 | 8/2003 | Blumenfeld et al. | |
| 2005/0105447 A1 * | 5/2005 | Ikenaka et al. ............ | 369/112.06 |
| 2006/0017001 A1 | 1/2006 | Donders et al. | |
| 2008/0040737 A1 * | 2/2008 | Jutte et al. .................... | 720/681 |

FOREIGN PATENT DOCUMENTS
EP 0286368 A2 10/1988

OTHER PUBLICATIONS

Sinzinger et al., Astigmatic Gradient Index Elements for Laser Diode Collimation and Beam Shaping, Oct. 10, 1995, Applied Optics, vol. 34, pp. 6626-6632.*

* cited by examiner

Primary Examiner — Christine Sung

(57) ABSTRACT

An optical system for illuminating a sample with a line beam includes a light source, a beam shaper for transforming the beam of light emitted by the light source into an intermediate astigmatic image, and an imaging system for transforming the intermediate astigmatic image into a final astigmatic image and for illuminating the sample. The beam shaper provides different non-unity magnifications in a lateral plane and in a transversal plane, and comprises a toroidal entrance surface for implementing the angular magnification and angular reduction and a toroidal exit surface with finite radii of curvature.

12 Claims, 6 Drawing Sheets

OPTICAL ILLUMINATION APPARATUS FOR ILLUMINATING A SAMPLE WITH A LINE BEAM

FIELD OF THE INVENTION

The invention relates to an optical system and method for illumination a sample as well as a detection device that includes the illumination system and a detection method including the illumination method. The optical illumination and the detection system is applicable in fluorescence detection systems and methods for analytical purposes.

BACKGROUND OF THE INVENTION

An example of the use of fluorescence detection is in nucleic acid testing (NAT). This is a core element in molecular diagnostics for detecting genetic predispositions for diseases, for determining RNA expression levels or identification of pathogens, like bacteria and viruses that cause infections.

In many cases, particularly in the identification of pathogens, the amount of target DNA present in a reasonable sample volume is very low, and this does not allow direct detection. Amplification techniques are necessary to obtain detectable quantities of the target material. Different amplification techniques have been proposed and are used in daily practice. The most widely used are based on the so-called Polymerase Chain Reaction (PCR).

The amplification involves the denaturing of double-stranded DNA at elevated temperature (typically >90 degrees Celsius), specific binding of primers to the DNA sample at a reduced temperature (approximately 65 degrees) and copying of the original sequences starting from the primer position (at approximately 70 degrees). This procedure is repeated and in every cycle the amount of DNA with the specific sequence is doubled (when proceeding at 100% efficiency).

After amplification, the presence of target DNA is detected by measuring the fluorescence intensity of the labeled amplified DNA, for instance after electrophoretic separation in a capillary or after hybridization to so-called capture probes which are applied in spots on a surface over which the amplification product is flowed.

This invention relates to an apparatus used to provide the illumination to the sample, and the method of use.

The standard technique for fluorescence detection is the use of a scanning confocal microscope. Typically, a small (<1 µm), diffraction limited spot is used to excite the fluorescence in the focal plane. In the detection part of the system, only the light resulting from this single excitation point is detected.

It has previously been proposed that the excitation of a number of spots or a complete line in parallel enables an increase in the scanning speed, without a major impact on the confocality of the detection system. A pixellated detector can be used to detect the fluorescent emission.

In order to generate the excitation beam for a confocal line scan, it has been proposed to modify an optical device for making a scan with a focused spot by adding an optical element such as a cylinder lens, that adds so-called astigmatism. If the cross-section of a beam is defined as the xy-plane, then each ray in the beam is characterized by coordinates (x,y). The beam is astigmatic if the rays on the x-axis, coordinates (x,0) have a different focus from the rays on the y-axis, coordinates (0,y).

SUMMARY OF THE INVENTION

The generation of astigmatism with an extra component, such as an cylinder lens, adds complexity and cost to the solution described hereinbefore. It is the aim of this invention to combine a number of functions in a single optical element to provide an improved solution.

According to a first aspect of the invention, there is provided an optical system for illuminating a sample with a line beam.

The invention enables the use of existing beam shaping apparatus, normally used to make a light output have a more circular cross section, in combination with the imaging system which illuminates the sample, in order to provide line beam inspection or analysis of a sample.

The optical system preferably comprises means for scanning the line beam across the sample. The invention thus allows for a much smaller and more compact scanning system with line illumination based on the reuse of standard optical storage components within the optical system.

This more compact optical system enables a completely miniaturized light path based on the confocal optics and light path used in a CD or DVD system with a minimal number of changes with respect to a standard DVD light path. This enables a solution that can be easily fabricated on existing DVD production lines.

The ratio of the length of one of the focal lines of the final astigmatic image and the distance between the beam shaper and the position of the beam shaper for which the astigmatic distance of the intermediate image is zero is preferably given by:

$$\frac{NA(M_x^2 - M_y^2)}{\sqrt{1 - NA^2/n^2} \; M^2},$$

where n is the refractive index of the sample medium, NA is the exit numerical aperture of the imaging system, M is the magnification of the imaging system and $M_x$ and $M_y$ are a first and second magnification of the beam shaper for the two focal lines of the intermediate image.

The final astigmatic image preferably comprises a line focus, as explained above. The width of the line can be diffraction limited, so that a confocal imaging system is provided. For example, the system can comprise a confocal microscope based on absorption, reflection luminescence or a combination of these. The light source may comprise a laser diode, but any other light source such as a light emitting diode or the like may be used without departing from the invention.

According to a second aspect of the invention there is provided a detection device incorporating the illumination system according to the invention and a detection system. In one embodiment the detection device is separate from the illumination system. Thus, the detection system may be located on an opposite side of the sample/substrate as the illumination system and they may make use of separate optics and components. Hence, advantageously, both sides of a substrate can be used to optically access a sample within the substrate.

In another embodiment the illumination system and collection arrangement of the detection device can share an excitation/collection lens, and the detector can comprise an imaging lens which focuses onto the detection surface. This provides a compact detection device benefiting amongst others from the advantageous offered by the illumination system. It may be more robust and cheap due to lesser parts and less complicated construction.

According to a third aspect of the invention there is provided an illumination method of illuminating a sample with a line beam. The method allows line illumination using simple CD and DVD optics as described hereinbefore.

According to a fourth aspect of the invention there is provided a detection method using the illumination method of the invention in conjunction with a detection method according to which light emitted from the sample and generated by the line beam is collected and detected. Thus, in this detection method, the line beam is used to illuminate the sample such that the light beam interacts with the sample. After interaction the by this illumination light generated light emanating from the sample and emitted from the sample is collected and detected. The term 'generated light' is herein understood to include light of the light beam that remains after absorption or scattering of part of the light beam by the sample to be analyzed, i.e. in the interaction herein is absorption or scattering of light by the sample. This remaining light to be collected may be collected and detected using a transmission or reflection setup as known to those skilled in the art. Hence in this case the detection method measures for example absorption using line illumination. Furthermore, the term 'generated light' is understood to include luminescence which is generally known to cover fluorescence and phosphorescence. In the latter case the detection method measures light resulting from excitation of the sample by the line beam.

The method may include that the substrate or sample is scanned.

BRIEF DESCRIPTION OF THE DRAWINGS

Examples of the invention will now be described in detail with reference to the accompanying drawings, in which.

DETAILED DESCRIPTION OF EMBODIMENTS

The invention relates to an optical system for illuminating a sample with a line beam. A beam shaper transforms the beam of light emitted by the light source into an intermediate astigmatic image, and an imaging system transforms the intermediate astigmatic image into a final astigmatic image and illuminates the sample. The beam shaper provides different non-unity magnifications in a lateral plane and in a transversal plane, and comprises a toroidal entrance surface and a toroidal exit surface, each with finite radii of curvature.

Methods and devices are known for detecting fluorophores in a device by exciting the fluorophores by light radiation through an objective lens and collecting the fluorescence, for example through the same lens in a reflective mode. The fluorescence radiation is projected onto a sensor device after having passed a filter device to select the appropriate wavelength range. The lens can be moved in a controlled way in three directions by different actuation means, to enable scanning over a sample of interest. A confocal imaging arrangement is typically used.

Figure 1:
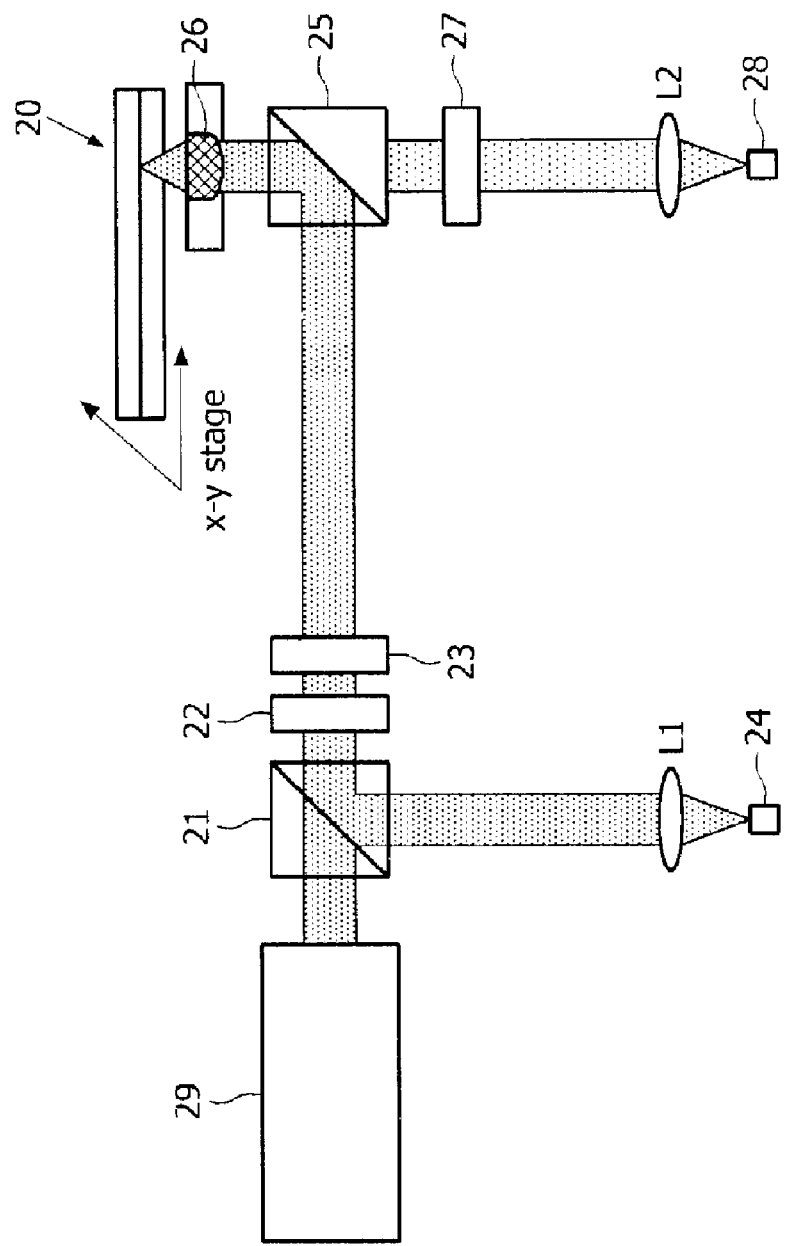
FIG. 1 shows a known fluorescence scanner based on a DVD optics system.

FIG. 1 shows the basic components of a known fluorescence scanner based on a DVD optical system. The sample to be investigated is confined into a given volume within a substrate 20.

The light generated by a light source 24 such as a laser is used to excite fluorescence. The light is collimated by a collimator lens L1 and subsequently focused in the sample by means of an excitation lens 26.

The lens 26 can move relative to the sample, preferably in all three dimensions. This relative motion can be decoupled arbitrarily, for example the sample can move in to the x-y plane and the lens in the z direction. Alternatively, the sample can be kept fixed and the lens has all the three-degree of freedom (x-y-z) on its own. Any other arrangement is also possible.

The laser light is reflected by a polarization beam splitter 21, i.e. a polarization dependent reflector, and is passed through a quarter wave plate 22 and a first band pass filter 23.

A dichroic beam splitter 25, i.e. a wavelength dependent reflector, directs the laser light to the excitation lens 26.

The induced fluorescence, as a result of the excitation light focused into the sample, is collected by a collection lens, which in this example is the same component as the excitation lens 26, and is directed toward a detector 28.

Any reflected unabsorbed laser light is reflected again by the beam splitter 25, whereas the fluorescence is passed through the beam splitter 25. A second band pass filter 27 provides further filtering, and the light is then focused on the detector 28 by an imaging lens L2 which images the sample onto the detector 28.

Many different types of detector can be used such as a photon tube multiplier, avalanche photon detector, CCD detector or photodiode detector. Preferably a detector offering spatial resolution is used such as a pixellated detector. This allows line detection and obviates scanning of the detector over the an illuminated region by the line beam.

For confocal imaging, the excitation volume is kept to a minimum, ideally to the diffraction limited spot that the excitation lens 26 can create. A typical confocal volume is in the order of a cubic micron, depending on the strength (numerical aperture, NA) of the excitation lens 26. The fluorescence created in this volume is collected by the collection lens and is imaged on the detector. In a confocal method, the focal point is confocal with a point in the detection path. At this point in the detection path, a small pinhole is typically placed to filter out any light coming from a location other than the focal point.

The light passing the pinhole is directed toward the detector. It is possible for the detector itself to play the role of the pinhole, with the restriction that the lateral size of the detector has to match the size of the focal point scaled by the focal length of the collection lens 26 divided by the focal length of the imaging lens L2.

This confocal mode is best suited to investigate a surface immobilization assay, as the result of an endpoint bio-experiment. The surface is scanned to analyze the full sample.

The lateral dimensions of the detector are designed taking into account the fields of the collection lens 26 and the imaging lens L2.

A control arrangement 29 keeps the focus of the objective lens precisely at the inner surface of the analytical device; a surface of the volume within the substrate 20 which is in contact with the analyte, while scanning the same surface. The focus of the objective lens can also be offset on purpose.

The invention can be implemented as a modification to the system of FIG. 1, which is adapted to provide an excitation beam in the form of a confocal line, rather than a confocal spot. Preferred examples of the invention are again based on standard DVD (or DVD/CD) optics.

In a preferred example of the invention, a standard beam shaper is used at the output of the laser source, and this is normally used to make the intensity distribution within the cone of light emitted by the laser more symmetric. However, in the system of the invention, the beam shaper is positioned differently with respect to the laser to generate a required amount of astigmatism. This can then be arranged to result in a narrow diffraction limited line in the focus of the collection lens 26 instead of the normal diffraction limited circular spot.

The use of a conventional beam shaper enables the optical system to be based on the optics of a standard CD/DVD player/writer. The known optical system is shown schematically in FIG. 2, and where components correspond to those in FIG. 1, the same reference numerals are used.

For a DVD reader, a red laser diode 24 is used. The intensity distribution over the angles within the emitted cone of light is very asymmetric; the angular width in one direction orthogonal to the optical axis is a factor two to three larger than the width in the other direction orthogonal to the optical axis. This asymmetry is compensated with a beam shaper 30.

The beam shaper 30 has an entrance surface, an exit surface located opposite thereto and an optical axis which coincides with the Z axis of a three-axis rectangular XYZ system of coordinates. The beam shaper 30 is for converting a beam having a first ratio between a first angular aperture in the YZ plane of the system of coordinates and a second, smaller angular aperture in the XZ plane into a beam having a second, smaller ratio between said angular apertures, said element realizing different angular magnifications in said two planes.

Thus, the beam shaper is designed to alter the elliptical output of the laser into a more uniform circular output.

The beam shaper used in the system of the invention preferably provides an angular magnification in a lateral plane and an angular reduction in a transversal plane.

The difference between the angular magnifications realized by the beam shaper 30 in the transversal plane on the one hand and the lateral plane on the other hand is substantially entirely realized by the entrance surface which changes the divergence of the beam, both in the transversal plane and in the lateral plane. If the beam shaper is arranged in a medium having a refractive index n1 and if the refractive index of the material of this element is n2, the angular reduction in the transversal plane is n1/n2 and the angular magnification in the lateral plane is n2/n1 and the beam-shaping power is approximately $(n1/n2)^2$.

Since the two virtual images formed by the entrance surface are located at different positions along the Z axis, the exit surface should have a slightly toroidal shape so as to combine these images to one image. The radius of curvature in the XZ plane is larger than that in the YZ plane. Toroidal is understood to mean that the radius of curvature of the surface in the lateral plane differs from that in the transversal plane.

The entrance surface is centrally provided with a substantially cylindrical portion whose cylindrical axis is parallel to the Y axis and introduces the angular reduction in the YZ plane and the angular magnification in the XZ plane. The beam-shaping power is now constituted by two components being angular magnification n2/n1 in the lateral plane and angular reduction n1/n2 in the transversal plane. Each of these components can be realized with less stringent tolerance requirements than those which apply to a beam shaper in which the beam shaping is realized in only one of these planes.

A possible beam shaper is described in more detail in U.S. Pat. No. 5,467,335, which is incorporated herein by way of reference.

A grating 32 is placed in the beam path in order to generate satellite spots.

A polarizing beam splitter 21 reflects the light and a collimator lens L1 is used to form a collimated beam. This is reflected by a folding mirror 34, a quarter wave plate 22 converts the linearly polarized light into circularly polarized light and this light is then focused by the lens 26 onto the data layer, within a substrate 20. Of course, for the optical system to be used in a medical diagnostic apparatus, the data layer becomes the surface on which immobilization of capture probes occurs.

The light is then reflected and collected by the same collection lens 26. The light then passes through the quarter wave plate 22 again, resulting in linearly polarized light that is perpendicular to the original polarization. Via the folding mirror 34, the light is focused by the collimating lens L1.

The light then passes through the polarizing beam splitter 21. The light then mostly passes through a dichroic mirror 36. The servo imaging lens L2 adds some astigmatism that is used in combination with a focus and tracking detector 40 to generate the focus error signals in order for steering and/or positioning the focus and therewith provide feedback during for example scanning of a sample or substrate.

The light path for CD light is nearly identical to the DVD path described above. When a CD is to be read out, the DVD laser is switched off and an infrared laser diode 43 in combination with a beam shaper 44 provides the illumination light. A grating 42 is again used to generate the satellite spots. The light is largely reflected by the dichroic mirror 36 and then passes largely through the polarizing beam splitter 21. Again, the light is focused on the data layer via lens 26. The reflected light is again collected by lens 26. This light again passes partly through the polarizing beam splitter 21 and the dichroic beam splitter 36 and is again imaged on the focus and tracking detector 40.

In one example of the invention, the beam path is modified such that it becomes suitable for sensitive fluorescence detection. As mentioned above, when sufficient laser power is available, it is advantageous to spread the excitation light over a larger area to improve the throughput and increase the total detected signal without compromising confocality. To this end, the normally circular diffraction limited spot can be elongated in one direction while remaining diffraction limited in the perpendicular direction.

This can be done by adding some type of astigmatism to the beam entering the lens 26.

The applicant has considered different methods for introducing this astigmatism, for example via a cylinder lens or a phase plate. A phase plate can be used to provide a linear array of focus spots or a solid illumination line, and a cylinder lens can be used to provide a solid illumination line.

In one example of the invention, the beam shaper 30 described above is moved along the optical axis. No special component is required to implement this. The position of the beam shaper is typically already fine-tuned during assembly and has the possibility to slide back and forth.

The invention thus uses displacement of the beam shaper of an optical pickup-unit such that the exit beam is focused into a line that can be scanned across a plane. The beam shaper in the system of the invention can be considered to transform the beam of light emitted by the light source into an intermediate astigmatic image, and the imaging system; e.g. the combination of collimator lens and objective lens can then be considered to transform the intermediate astigmatic image into a final astigmatic image.

An astigmatic image of a (light emitting) point is defined as consisting of two focal lines that are mutually perpendicular and perpendicular to the optical axis and that are separated along the optical axis over a certain distance, the astigmatic distance. The sample is scanned with one of the two focal lines in a direction substantially perpendicular to the line and to the optical axis. The length of the focal lines is proportional to this astigmatic distance. If the astigmatic length goes to zero, so will the length of the two focal lines, meaning that the lines will coalesce into a single point.

To implement the beam shaping functions described above, the beam shaper has a first refractive surface with curvature radii along a first and second direction perpendicular to an optical axis that are substantially different, a second refractive surface with curvature radii along a first and second direction perpendicular to an optical axis that are substantially different, a thickness and a refractive index.

There is generally a first position of the beam shaper with respect to the light source for which the astigmatic distance of the intermediate image is zero. The beam shaper is positioned with respect to this first position. In particular, the position of the beam shaper with respect to the light source is displaced with respect to the first position by a distance Δv given by:

$$\Delta v = \frac{L\sqrt{1 - NA^2/n^2} \, M^2}{NA(M_x^2 - M_y^2)}$$

where L is the length of (one of) the focal lines of the final astigmatic image, NA is the exit numerical aperture of the imaging system, n is the refractive index of the sample, and Mx and My are a first and second magnification of the beam shaper pertaining to the two focal lines of the intermediate image.

The magnification is defined as sin α/sin β, where α and β are the largest ray angles in the system; α is the input ray angle, and β is the output ray angle. The numerical aperture is defined as sin α for the entrance numerical aperture, and sin β for the exit numerical aperture. If the object and/or image side is in a medium with refractive index n then the numerical aperture is n×sin α or n×sin β, respectively.

In this arrangement, the length of the focal line that is used for scanning can be adapted to the requirements of the scanning process by changing the position of the beam shaper. Thus, a single optical design is suitable for multiple types of scanning devices.

Moving the beam shaper 30 to control the shape of the excitation beam will however also induce some defocus. This may not cause any problem. However, it can in any case be compensated by either moving the position of the laser 24 or in a preferred embodiment this is done by changing the optical thickness of a component replacing the grating 32.

Figure 3:
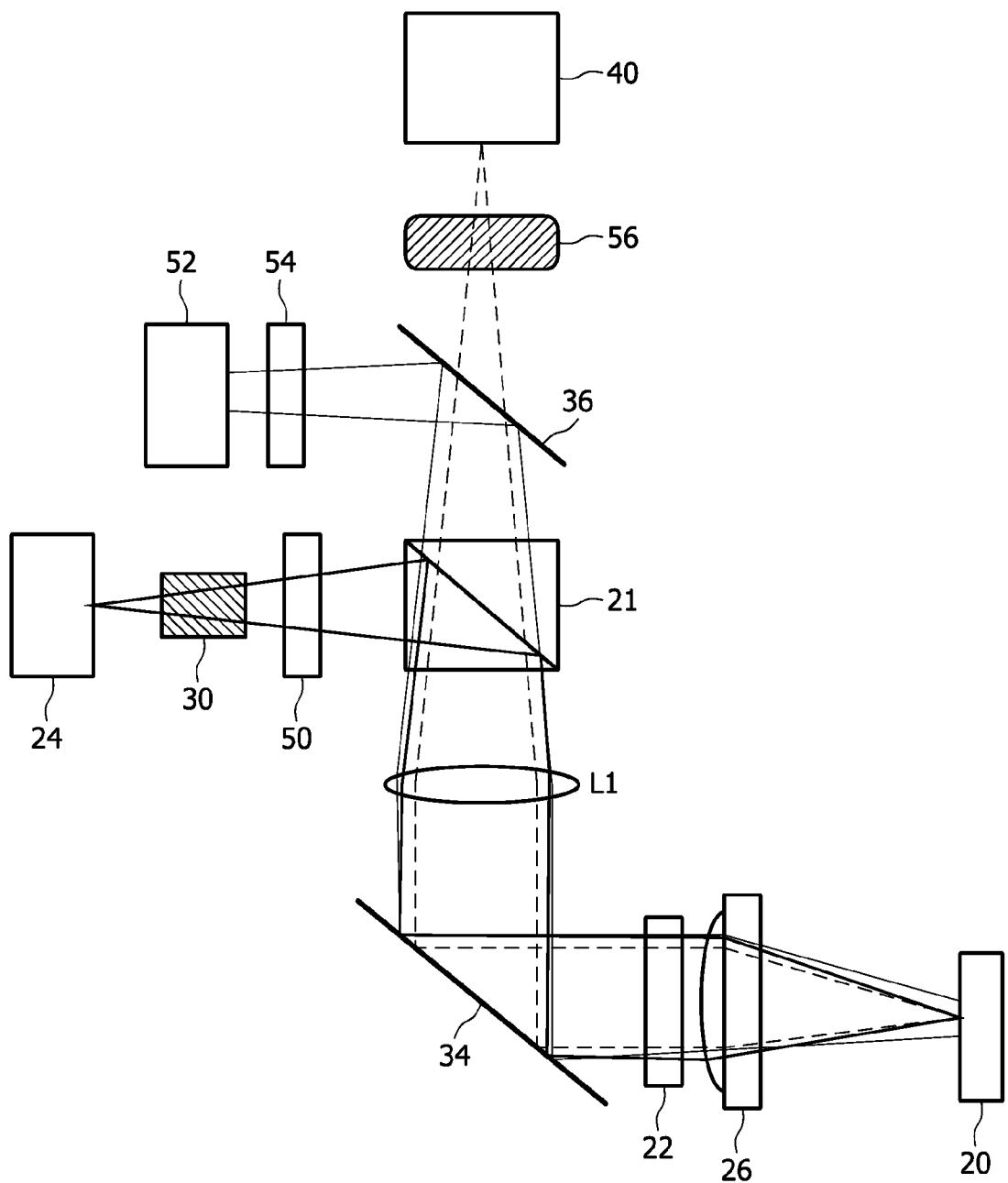
FIG. 3 shows a first example of confocal scanner using an optical scanning apparatus of the invention.

FIG. 3 shows the light path which arises in a first example of system of the invention, used for fluorescence excitation and detection. Most components remain the same and are given the same reference numbers. The beam shaper is the same as the normally used but it is moved forward. The grating 32 that generates the satellite spots is replaced by a bandpass filter 50 that will spectrally purify the laser light. The thickness of this filter can be used to fine tune the defocus induced by the movement of the beam shaper.

By moving the beam shaper 30, the light after the collimating lens will have a fairly large astigmatism. In one direction the light "is parallel" whereas the perpendicular direction is slightly diverging. This results after the objective lens 26 in a line focus.

On the surface of the sample fluorescence will be generated. This fluorescence light is collected by the objective lens 26 and passes partly through the polarizing beam splitter 21. The dichroic mirror 36 reflects most of the fluorescent light towards a detector 52 after passing through an additional filter 54 to reject the remaining excitation light. The detector is preferably implemented as a pixellated detector. The dichroic mirror can be the same as in FIG. 2, or a different mirror can be used that is optimized to reflect the fluorescence.

The reflected excitation light still passes through the dichroic mirror 36. A modified servo lens 56 is used to correct for most of the earlier induced astigmatism. The residual astigmatism can be used in combination with a (standard) quadrant detector 40 to generate the focus error signals.

The direction of the line in the focus plane is arranged to be perpendicular to the fast scan direction. This can be achieved by rotating the laser and beam shaper assembly, or by rotating the complete OPU with respect to the axis of movement.

In the return path of the reflected light the astigmatism in the beam is nearly completely compensated by the servo lens 56. The remainder of the astigmatism is used in combination with a standard quadrant detector 40 to generate the auto focus error signals. The residual astigmatism of light beam means that a change in the focus position will change the relative contribution of the light falling on the different quadrants of the detector. From these signals an autofocus error signal can be derived.

Figure 4:
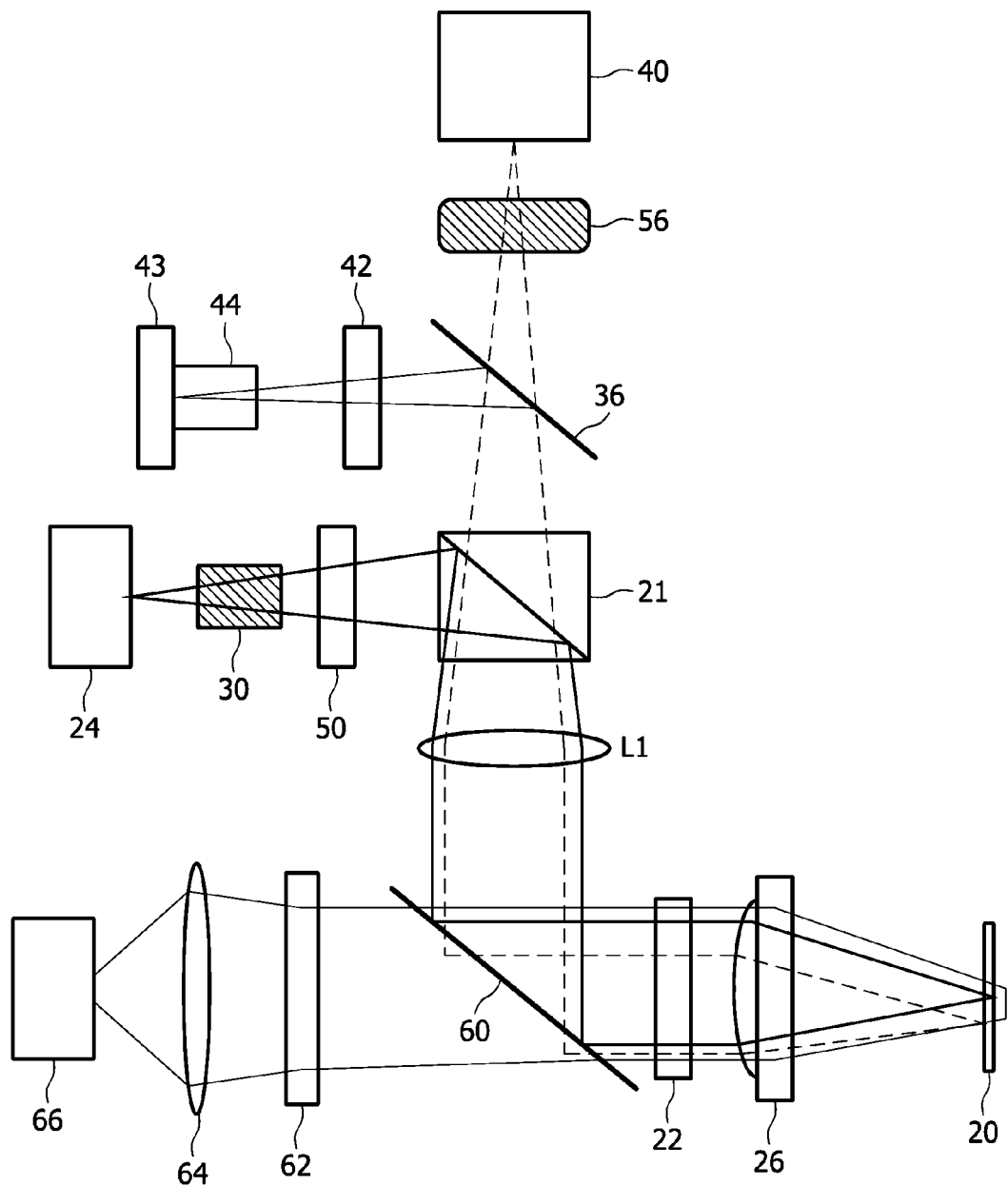
FIG. 4 shows a second example of confocal scanner using an optical scanning apparatus of the invention.

A second embodiment of a device according to the invention is shown in FIG. 4. The same excitation method is used as in FIG. 3, but the detector is moved to a different position. By replacing the folding mirror 34 by a dichroic mirror 60, the fluorescent light can be transmitted by this element. Behind the dichroic mirror, the light is filtered with a filter 62 and is then focused by a lens 64 on the detector 66.

Figure 2:
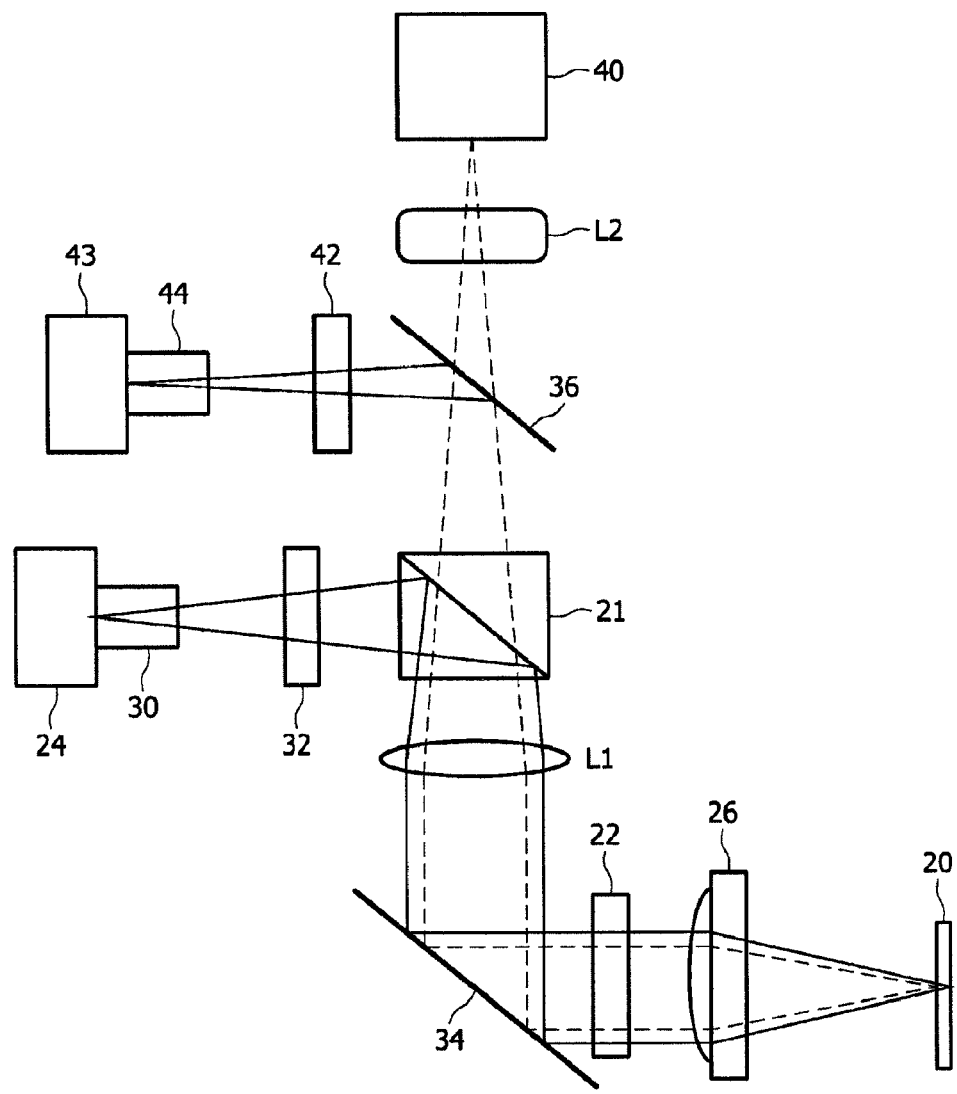
FIG. 2 shows in more detail a known CD/DVD optical pickup arrangement.

This embodiment requires more modifications with respect to the DVD light path described with reference to FIG. 2. The sensitivity of this embodiment will however be better than that of FIG. 3 since the fluorescence light is not split into two parts at the polarizing beam splitter 21. Furthermore, in this embodiment it is possible to place the filter 62 in a parallel part of the beam. When interference filters are used this will result in a better rejection of excitation light resulting in a reduced background noise.

In a standard OPU, the glue that usually fixes the beam shaper can simply be removed, such that the position can be moved back and forth towards the laser. The system of the invention has been tested and found to provide the required elongation of the confocal excitation beam simply by adjusting the relative positions of the beam shaper and laser in the standard OPU.

Two examples have been described above based on the adaptation of DVD/CD optics. The invention is not limited to this approach. FIG. 5 shows a number of embodiments based on the different combinations of components which can be used to implement the current invention.

Figure 5A:
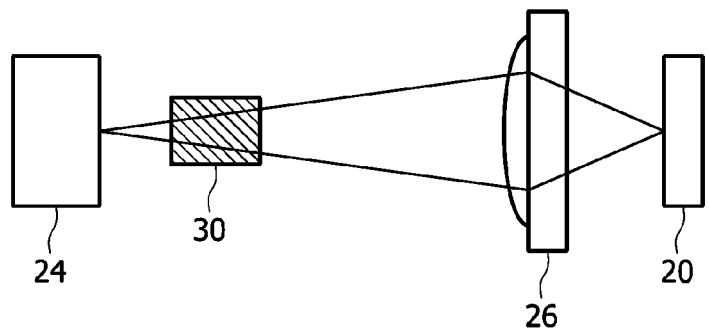
FIGS. 5a to 5c show further examples of optical scanning apparatus of the invention.

If only a line illumination mode is desired, a simplest embodiment shown in FIG. 5a can be used. The numbering of the components is the same as used in FIG. 3 and FIG. 4, and the system comprises the beam shaper 30, laser 24 and lens 26. Line illumination can be used in systems other than for fluorescence detection, such as scanning microscopes for instance to measure cells or pathology slides.

Figure 5B:
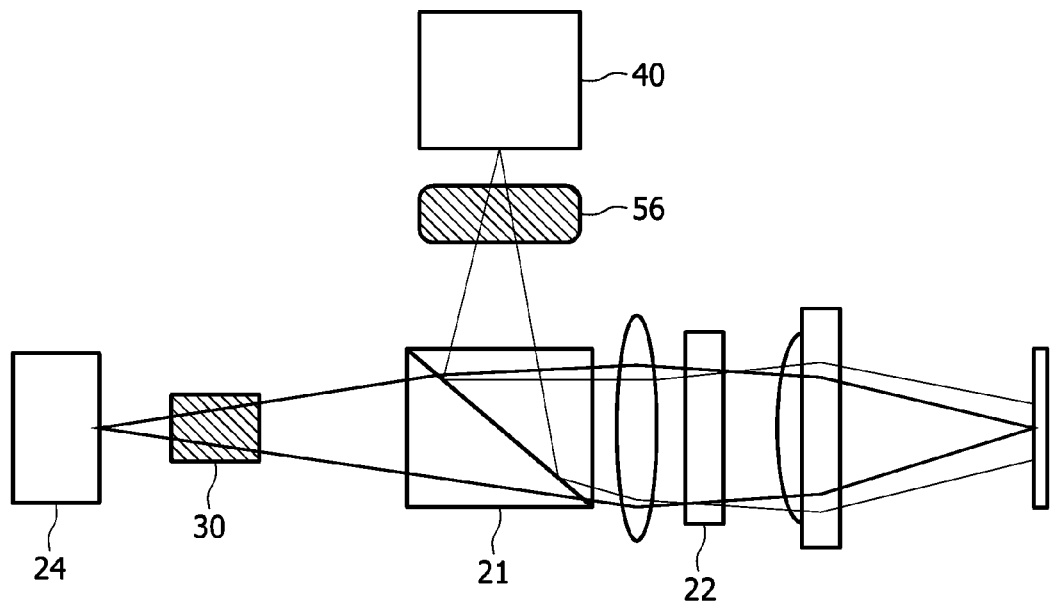

An autofocus system is added to form the system shown in FIG. 5b, which uses a polarizing beam splitter 21 in combination with a quarter wave plate 22 to separate the excitation and reflected light.

Figure 5C:
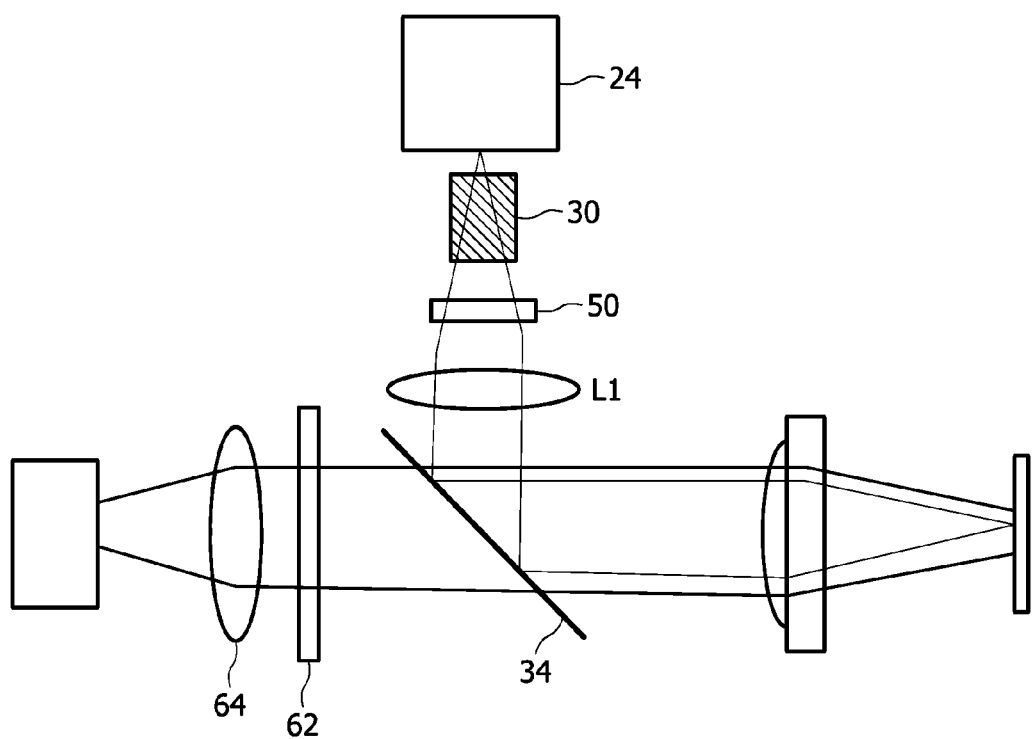

In order to combine line illumination with fluorescence detection, the addition of a dichoric mirror 34 is required as shown in FIG. 5c, in combination with filters 50 and 62 to separate the excitation light from the fluorescence.

The invention provides modification of the beam path such that it becomes suitable for sensitive fluorescence detection in combination with a line illumination mode. In the preferred implementation, the "standard" beam shaper is shifted to solve this problem. There are, however, other ways to solve this same problem.

Two examples are explained below:

(i) The standard collimator shown in FIG. 4 as L1 can be replaced with a new dedicated component, to implement the beam shaping function, and thereby replace the beam shaper 30.

(ii) The beam shaper can be replaced by a new dedicated component that adds the required astigmatism to excitation beam. This may be provided at the output of the laser diode, which can already include an integrated beam shaper.

In the example above, the lens 26 is used both for the excitation light and the fluorescence light, and it can also be used for focus and tracking signals. Separate lenses may be used for the excitation light and the fluorescence light, for example with non-normal directions of illumination, or with operation in a transmissive mode.

The invention is not limited to the examples described herein. Various modifications exist. Thus, for example, the invention is described with reference to a sample that fluoresces by means of fluorophores. However, the invention may in general be used in devices that generate in a general way an optical signal. Thus samples may be measured that absorb part of the illuminating line beam so that the remaining line beam light is collected and provides a clue with respect to constitution of a sample with respect to presence, identity and/or concentration of one or more of its constituents or added substances that facilitate the constituents detection such as for example label substances. Likewise the effect of reflection of the line beam caused by the sample may be used in the detection process. Alternatively, the line beam may function as an excitation source in order to excite one/or more of the constituents of the sample or the added substances so that luminescence radiation results that can be collected and detected. Herein luminescence is meant to include fluorescence and/or phosphorescence.

In generally, the invention relates to the generation of a line for illumination of a sample. The illumination line is of advantage in a detection device as described hereinbefore. The invention is of particular interest for line scanning or confocal line scanning in order to speed up the detection process. In some cases, scanning to cover an area of a surface may however not be required. The invention will also then provide its advantages.

The invention is in general applicable in the field of sample analysis wherein samples need to be examined volumetric or on a surface. The application of the invention may thus be in analytical methods requiring line excitation. These also include analysis on gaseous, liquid and/or solid samples.

Thus the invention may be used for chemical analysis of samples such as to determine their constitution or it may be used to inspect the evolvement or progress of a chemical or biochemical or biological process. Improved scanning speed enables the collection of more data points per time unit resulting in improved dynamic measurements.

Without being limited to the field of bioanalysis, the preferred application of the invention is in the field of molecular diagnostics based on the detection of for example nucleic acids after amplification, proteins or other biochemical or biological entities. Further preferred fields of application include, clinical diagnostics, point-of-care diagnostics, advanced bio-molecular diagnostic research and optical bio-sensors, in particular related to DNA detection in combination with amplification methods, such as PCR, q-PCR, etc. The invention can also be used as a line scanner for imaging cells and/or tissue for example for pathology purposes. The can also be used for detection in an immunoassay to detect proteins.

The above-mentioned embodiments illustrate rather than limit the invention, and at that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the device claim enumerating several means, several of these means may be embodied by one and the same item of hardware. The mere fact that certain measures are recited in mutually different dependent claims does not indicate that the combination of these measures cannot be used to advantage.

The invention claimed is:

1. An optical system for illuminating a sample with a line beam, the system comprising:
   a light source;
   a beam shaper for transforming the beam of light emitted by the light source into an intermediate astigmatic image by changing a position of the beam shaper relative to the light source; and
   an imaging system for transforming the intermediate astigmatic image into a final astigmatic image and for illuminating the sample with the line beam,
   wherein the beam shaper provides different non-unity magnifications in a lateral plane and in a transversal plane, and comprises a toroidal entrance surface and a toroidal exit surface, each with finite radii of curvature.

2. The optical system as claimed in claim 1, wherein the final astigmatic image comprises a line focus.

3. The optical system as claimed in claim 2, wherein a width of the line beam is diffraction limited.

4. An optical system as claimed in claim 1, wherein a ratio (a) of a length of one of focal lines of the final astigmatic image to (b) a distance between the beam shaper and the position of the beam shaper for which an astigmatic distance of the intermediate image is zero is given by:

$$\frac{NA(M_x^2 - M_y^2)}{(M^2)\sqrt{1 - \frac{NA^2}{n^2}}}$$

where n is a refractive index of the sample, NA is an exit numerical aperture of the imaging system, M is a magnification of the imaging system and $M_x$ and $M_y$ are a first magnification and a second magnification of the beam shaper for the two focal lines of the intermediate image.

5. The optical system of claim 1, wherein the beam shaper is moveable back and forth towards the light source to provide a desired elongation of the line beam.

6. A detection device, comprising:
   an optical system for illuminating a sample with a line beam, the system comprising:
   a light source;
   a beam shaper for transforming the beam of light emitted by the light source into an intermediate astigmatic image by changing a position of the beam shaper relative to the light source; and an imaging system for transforming the intermediate astigmatic image into a final astigmatic image and for illuminating the sample with the line beam, wherein the beam shaper provides different non-unity magnifications in a lateral plane and in a transversal plane, and comprises a toroidal entrance surface and a toroidal exit surface, each with finite radii of curvature;

an optical collection arrangement for collecting light emitted from the sample and generated by the line beam and;

a detection system for detecting the collected light.

7. The detection device as claimed in claim 6, wherein the imaging system and the optical collection arrangement share an excitation/collection lens.

8. The detection device as claimed in claim 6, wherein the detection system comprises an imaging lens which focuses onto a detection surface of the detection system.

9. The detection device as claimed in claim 6, wherein the light emitted from the sample and generated by the line beam comprises luminescence light.

10. The detection device of claim 6, wherein the beam shaper is moveable back and forth towards the light source to provide a desired elongation of the line beam.

11. An illumination method for illuminating a sample with a line beam, comprising the acts of:
    generating a beam of light using a light source;
    transforming the beam of light into an intermediate astigmatic image using a beam shaper by changing a position of the beam shaper relative to the light source; and
    transforming the intermediate astigmatic image into a final astigmatic image using an imaging system for illuminating the sample with the line beam,
    wherein the beam shaper provides different non-unity magnifications in a lateral plane and in a transversal plane, and comprises a toroidal entrance surface and a toroidal exit surface, each with finite radii of curvature.

12. The illumination method of claim 11, wherein the beam shaper is moveable back and forth towards the light source to provide a desired elongation of the line beam.

\* \* \* \* \*